United States Patent [19]

Jassawalla

[11] 4,140,118

[45] Feb. 20, 1979

[54] CASSETTE CHAMBER FOR INTRAVENOUS DELIVERY SYSTEM

[75] Inventor: Jal S. Jassawalla, San Francisco, Calif.

[73] Assignee: Andros Incorporated, Berkeley, Calif.

[21] Appl. No.: 775,743

[22] Filed: Mar. 9, 1977

[51] Int. Cl.$^2$ .............................................. A61M 5/00
[52] U.S. Cl. ................................. 128/214 F; 417/435
[58] Field of Search ........... 128/214 R, 214 C, 214 E, 128/214 F, 214.2, 273; 417/435

[56] References Cited

U.S. PATENT DOCUMENTS

| | | | |
|---|---|---|---|
| 3,039,399 | 6/1962 | Everett | 128/DIG. 3 |
| 3,559,644 | 2/1971 | Stoft et al. | 128/214 F |
| 3,620,650 | 11/1971 | Shaw | 128/214 F X |
| 3,650,093 | 3/1972 | Rosenberg | 128/214.2 |
| 3,993,061 | 11/1976 | O'Leary | 128/214 F |
| 4,030,495 | 6/1977 | Virag | 128/214 F X |

*Primary Examiner*—Dalton L. Truluck
*Attorney, Agent, or Firm*—Fitch, Even, Tabin & Luedeka

[57] ABSTRACT

A cassette is described for use in an intravenous delivery system having a pump. The volume of a main chamber defined by the cassette body is varied and unidirectional inlet and outlet valves maintain the fluid direction into and out of the main chamber. In the operating position of the cassette, the outlet valve is positioned to be in communication with any gas present in the main chamber. For the purpose of accumulating air from the upstream portion of the intravenous delivery system in which the cassette is used, a prechamber is positioned above the inlet port communicating therewith.

3 Claims, 2 Drawing Figures

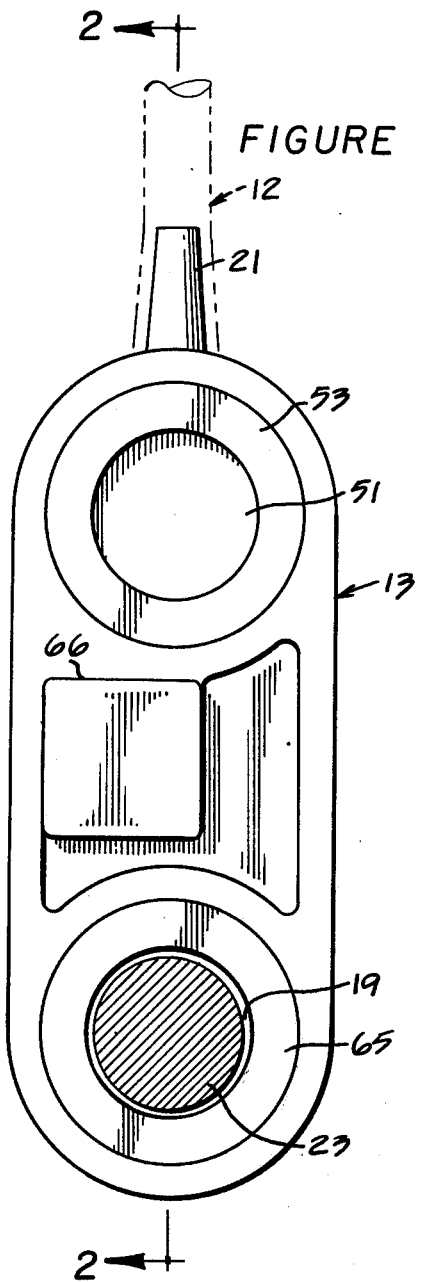
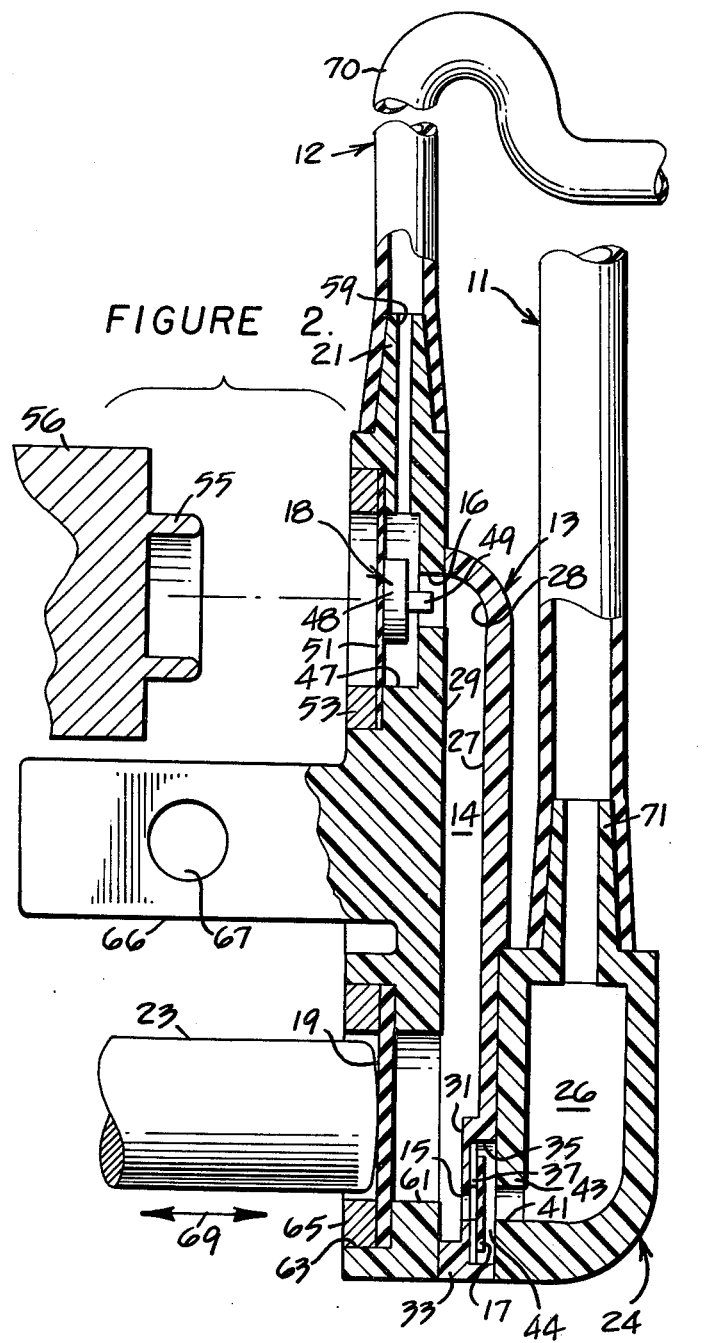
FIGURE 1.
FIGURE 2.

CASSETTE CHAMBER FOR INTRAVENOUS DELIVERY SYSTEM

The present invention relates to the field of medical fluid delivery systems and, more particularly, to intravenous delivery systems for the delivery of drugs, plasma, glucose solutions and the like.

Various systems for the delivery of fluids intravenously or intra arterially are well known in the prior art, and such systems are in widespread daily use in hospitals throughout the world. These systems (I. V. systems) are commonly used for the intravenous or intra arterial delivery of such fluids as glucose solutions and blood plasma, and for the delivery of drugs, all at controlled delivery rates depending on the patient's needs, and in the case of drugs, the drug concentration being delivered.

The oldest and most commonly used form of delivery system is comprised of a fluid container, a drip chamber and an adjustable clamp in the tube leading from the drip chamber to the needle penetrating the vein. The fluid container or bottle is supported at an elevated position with respect to the patient, with the drip chamber typically immediately thereunder. Transparent walls in the drip chamber coupled with a fixed volume of air therein allows the visual determination of the drip rate, which in turn is adjustable by the hose clamp. Thus, as fluid being delivered seeps past the pinched area of the hose, the air pressure in the drip chamber decreases, thereby encouraging the formation and dislodging of a drop from the tip of the small tube into the drip chamber coupled to the bottle. Such systems may be used alone, or the drip chamber used in conjunction with some other type of metering or pumping mechanism so that the visually observed drip rate may be used as a cross-check to verify the proper operation of the pumping device.

Another type of I. V. system which has come into substantial use in recent years utilizes what is commonly referred to as some form of a peristaltic pump. Such pumps are characterized by a length of flexible tubing which is disposed within an arc between a stator-like member and a rotor assembly. The rotor assembly is provided with a plurality of rollers which, upon rotation of the rotor assembly, successively pinch-off the tube and advance the location of the pinch-off so as to progressively advance the fluid within the tube at a rate determined by the rate of rotation of the rotor. Typically, such systems are driven in rotation by some form of motorgear assembly so as to provide the generally desired low pumping rate by the low speed rotation of the rotor. Such pumps have the advantage of having a disposable element in the fluid flow path, in that the length of tubing in the pump may be replaced after each use. In principle, the pumps also have the further advantage of providing the low and variable flow rates by way of a positive displacement pump. In practice, however, these systems characteristically exhibit poor accuracy and poor reproducibility. They are mechanically complex, and require a substantial amount of power, thereby making them relatively expensive and difficult to use on battery operation.

Another form of pump is the positive displacement pump wherein the volume of the pump chamber is varied by a relatively small amount at a certain rate, and check valves are provided at the inlet and outlet to provide the pumping action. By proper placement of inlet and outlet valves, such pumps may be operated so as to not pump air, thereby providing for automatic shut-off of the pump in the event of exhaustion of the supply of fluid being injected. Also, a pulse source may be used for operation to provide a variable pulse rate to thereby vary the pumping rate. However, in such pumps accumulation of air in the pumping chamber can result in deviations in flow accuracy of from a few percent to in excess of eighty percent.

An improved form of positive displacement pump is shown and described in copending U.S. Patent application Ser. No. 701,238 filed June 30, 1976, and entitled "Intravenous and Intra Arterial Delivery System". Said application is assigned to the assignee of the present invention. The system described in aforesaid patent application includes a pump and a detachable cassette used in connection therewith. The cassette includes a pumping chamber, the volume of which is varied by the pump. Inlet and outlet valves cause the intravenous fluid to enter and leave the chamber of the cassette. The present invention relates to an improved cassette design for use in a system of the general type described in the aforesaid patent application.

It is an object of the present invention to provide an improved intravenous delivery system.

Another object of the invention is to provide a low cost disposable cassette for use in an intravenous delivery system and which connects with a pump therein.

A further object of the invention is to provide a disposable cassette for use in an intravenous delivery system wherein very high pumping accuracy is achieved and wherein the danger of pumping air is minimized.

Other objects of the invention will become apparent to those skilled in the art from the following description taken in connection with the accompanying drawings wherein:

FIG. 1 is an elevational view of the side of the cassette of FIG. 1 which faces the pump; and FIG. 2 is a full section view of the cassette of the invention taken along the line 2—2 of FIG. 1 shown mounted with portions of a pump and other parts of the system illustrated schematically and exploded.

Very generally, the cassette of the invention operates between an upstream portion 11 and a downstream portion 12 of the intravenous delivery system in which the cassette is employed. The cassette includes a cassette body 13 with a main chamber 14 having an inlet port 15 and an outlet port 16. First valve means 17 are coupled to said inlet port for allowing unidirectional flow into said main chamber through the inlet port. Second valve means 18 are coupled to the outlet port for allowing unidirectional flow out of the main chamber through the outlet port. Movable means 19 vary the volume of the main chamber in response to motive power applied by the pump. The outlet valve is disposed so as to remain in communication with any gas present in the main cassette chamber. This enables the pump to continuously purge the main cassette chamber free of any gas that might enter it. In the embodiment shown in FIGS. 1 and 2, the outlet port is positioned to be at the top of the main chamber when the cassette is supported in operating position by the pump. Means 24 define a prechamber positioned above the inlet port and communicating therewith. The prechamber 26 has a volume selected to accumulate air from the upstream portion of the intravenous delivery system in an amount sufficient to maintain the chamber substantially air free.

Referring in greater detail to the drawings, the cassette body 13 is of generally elongated oval outline as viewed in FIG. 1, having semicircular end configurations. The internal surfaces of the cassette body facing on the chamber 14 are of similar outline with one of the surfaces 27 being blended into a radius 28 terminating at the other of the surfaces 29. The cassette body is formed of molded plastic in separate parts and welded together. The surface 27 has a step 31 formed at the lower end thereof which terminates spaced from the surface 29. The resulting space is closed by a horizontal lip 33.

The inlet port 15 is formed in the cassette body extending from the surface 27 at the step 31 adjacent the lower end of the chamber 14 as viewed in FIG. 2. A circular recess 35 is provided in the cassette body at the step 31 coaxial with the opening or inlet port 15. A plurality of ribs 37 are formed in the bottom surface of the recess 35 extending inwardly from the periphery thereof to adjacent the opening or inlet port 15. The valve means 17 comprise a disc which rests against the ribs 37, the disc being of smaller diameter than the diameter of the recess 35. The prechamber defining means 24 are secured against the cassette body and have an opening 41 coaxial with the inlet opening 15 formed in a portion 43 of the prechamber defining means 24. The portion 43 of the prechamber defining means extends over the recess 35 and forms a valve chamber 44 in which the disc 17 is movable between a position resting against the ribs 37 and a position resting flush against the portion 43. When the pressure inside the chamber 14 exceeds the pressure on the opposite side of the disc, the disc is pressed against the portion 43, thereby closing off the opening 41 which passes through the prechamber defining means 24 from the prechamber 26. When the pressure in the chamber 14 is lower than the pressure on the opposite side of the disc 17, the disc moves against the ribs 37, allowing flow around periphery of the disc, between the ribs, and through the inlet port 15. Thus, the valve means 17 operate to provide unidirectional flow into the chamber 14, but prevent backflow out of the chamber 14.

At the opposite end or top of the elongated main chamber 14, the outlet valve means 18 are positioned. The outlet valve means 18 are positioned in a generally cylindrical recess 47 formed in the cassette body coaxially of the outlet port 16. The valve means 18 include a head 48 which is movable to abut the outlet port 16, a guide stem 49 extending therefrom, and an integral resilient membrane 51 spanning the recess 47. The membrane 51 is stretched over the opening of the recess 47 and is held in place by a clamping ring 53. When the cassette is mounted to the pump, annular preloading means 55 on the pump 56 press against the membrane 51 biasing the head 48 of the valve means 18 against the outlet port 16 to close the outlet port off. Sufficient pressure within the chamber 14, however, will displace the head 48 against the bias of the membrane 51 and allow fluid flow past the valve means 18 and into the chamber 47.

The collector means 21, in the form of a nipple, include a passage 59 which communicates with the recess or chamber 47. Fluid can then flow through the passage 59 and into the downstream portion of the intravenous delivery system, illustrated by the tube 12.

The movable means 19 which are provided for varying the volume of the chamber 14, in the illustrated embodiment, comprise a membrane stretched across a circular opening 61 in the cassette body 13. The membrane 19 spans the opening 61 and the periphery thereof extends into a recess 63 of larger diameter. A clamping ring 65 seals the periphery of the membrane in the recess.

When the cassette is mounted to the pump, the actuator rod portion of which is shown at 23, coupling means are provided to thus secure the cassette in the proper position with respect to the pump. In its operating position, the outlet port 16 is at the top of the pumping chamber 14, as illustrated. The coupling means in the illustrated embodiment comprise a tongue 66 which extends into a suitable recess, not shown, on the pump. A detent 67 is provided on the tongue to be engaged by a suitable spring bias plug, not shown, to thus secure the cassette in position. The illustrated portion of the pump comprises a rod 23 which reciprocates in the direction of the arrow 69 and which has a rounded end engaging the membrane 19. The membrane is biased slightly inward at all times by the pump rod so that the amount of reciprocation of the rod accurately governs and is related to the amount of variance of the volume of the chamber.

In operating the illustrated cassette, movement of the rod 23 to the right of FIG. 2 causes diminution in the total volume of the chamber 14. This increases the pressure therein, biasing the disc 17 against the surface of the portion 43 to close the inlet port while at the same time urging the head 38 of the valve means 18 away from its position against the outlet port 16. Thus, fluid is allowed to flow through the outlet port and into the downstream portion 12 of the intravenous delivery system.

When the rod 23 moves to the left from the previously described position, the volume of the chamber 14 enlarges, thus reducing the pressure therein. This causes the valve means 18 to seal the outlet port 16 while at the same time allowing the disc 17 to seat against the ribs 37. Thus, fluid can flow through the inlet port 15.

A significant advantage of the foregoing described cassette is in the inability of air to accumulate in the chamber 14 and thus have a deleterious effect on the accuracy of the set pumping rate of the system. Any air in the chamber 14 results in a decrease in the pumping rate because of the compressibility of the air-liquid mixture and can be of considerable significance, depending on the amount accumulated. In many prior art designs such a decrease in the pumping rate may go undetected for sufficiently long periods of time so as to have caused serious problems. In the cassette of this invention, any air in the system is automatically expelled because the outlet port is at the top of the pumping chamber. In this respect, therefore, the cassette is continuously primed. Any danger from pumping air can be accommodated by an air trap 70 in the downstream portion of the system.

For the purpose of preventing air from entering the main chamber 14 of the cassette, the prechamber defining means 24 are provided. The prechamber 26 defined thereby is positioned above the inlet port 15 communicating therewith. A nipple 71 extends from the prechamber defining means 24 in vertical alignment with respect to the cassette operating position. The upstream portion 11 of the intravenous delivery system, shown by a portion of a tube, is coupled to the nipple 71. Air is frequently present in the upstream portion of a typical intravenous delivery system. Bubbles, which adhere to the sides of the tubing and other passages, have a tendency to agglomerate and thus migrate toward the cassette. Air may also enter the upstream portion of the intravenous delivery system through injection septums or slow leaks, particularly between the tubing and the drip chamber, not shown, commonly employed in intravenous delivery systems. The prechamber 26 effectively traps the air thus preventing it from entering the chamber 14. The volume of the prechamber 26 is selected depending upon the expected volume of air normally working its way down toward the cassette during the course of an intravenous delivery, and is preferably equal to or greater than the volume of the chamber 14. Thus, the volume of the prechamber 26 must be significant and the prechamber must be located at a level higher than the inlet port. Where the volume of the chamber 14 is of the order of two to three cubic centimeters, the volume of the prechamber 26 may be of the order of three cubic centimeters.

It may be seen, therefore, that the invention provides an improved cassette for use in an intravenous delivery system. The cassette is simple of construction and low in cost, and effectively prevents air from accumulating in the main chamber of the cassette, thus ensuring a constant and accurate rate of delivery of the intravenous fluid.

Various modifications of the invention in addition to those shown and described herein will become apparent to those skilled in the art from the foregoing description and accompanying drawings. Such modifications are intended to fall within the scope of the appended claims.

What is claimed is:

1. A cassette for use in an intravenous delivery system of the limited positive displacement type having a pump, said cassette operating between an upstream portion and a downstream portion of the intravenous delivery system and comprising, a cassette body having wall means defining an elongated main chamber, said wall means having an inlet port proximate end of said main chamber and an outlet port proximate the opposite end thereof, a first valve at said inlet port allowing unidirectional flow into said main chamber through said inlet port, a second valve at said outlet port for allowing unidirectional flow out of said main chamber through said outlet port, said cassette body having an opening in said wall means, a deformable membrane extending across said opening and affixed at its periphery to said wall means for varying the volume of said main chamber in response to deformation of said membrane, said cassette body having further wall means defining a prechamber positioned above said inlet port, said inlet port being interposed between said prechamber and said main chamber, said prechamber having a volume at least substantially equal to the volume of said main chamber to accumulate air from the upstream portion of the intravenous delivery system in an amount sufficient to maintain said main chamber air free, means for coupling said prechamber to the upstream portion of the intravenous delivery system, and means for mounting said cassette to a pump such that said outlet port is positioned at the uppermost end of said chamber to be in communication with any gas present in said main chamber with said cassette in operating position in the system and such that said inlet port is positioned at the lowermost end of said prechamber.

2. A cassette according to claim 1 wherein said prechamber defining means include means for coupling said prechamber to the upstream portion of the delivery system.

3. A cassette according to claim 1 including a tongue extending from said cassette body, said tongue having detent means thereon for coupling said cassette to the pump.

* * * * *

UNITED STATES PATENT AND TRADEMARK OFFICE
CERTIFICATE OF CORRECTION

PATENT NO. : 4,140,118
DATED : February 20, 1979
INVENTOR(S) : Jal S. Jassawalla It is certified that error appears in the above–identified patent and that said Letters Patent are hereby corrected as shown below:

Column 1, line 48, after "tube" insert ---along the tube---.

Column 4, line 28, change "38" to ---48---.

Column 5, line 36, after "proximate" insert ---one---.

Signed and Sealed this

Tenth Day of July 1979

[SEAL]

Attest:

Attesting Officer

LUTRELLE F. PARKER
Acting Commissioner of Patents and Trademarks